United States Patent [19]

Shettigar

[11] Patent Number: 4,955,857
[45] Date of Patent: Sep. 11, 1990

[54] MULTI-ENZYME BIOREACTOR THERAPY FOR CANCER

[76] Inventor: Udipi R. Shettigar, 1021 Medical Plz. South, Salt Lake City, Utah 84112

[21] Appl. No.: 231,133

[22] Filed: Aug. 10, 1988

Related U.S. Application Data

[63] Continuation-in-part of Ser. No. 220,544, Jul. 18, 1988.

[51] Int. Cl.⁵ ............................................. A61M 37/00
[52] U.S. Cl. ............................................ 604/5; 604/4;
604/28; 530/412; 210/195.2; 210/259; 210/632;
210/500.23
[58] Field of Search ............... 604/4, 5, 28; 435/815;
530/412, 413, 415, 416; 210/259, 632, 500.23,
195.2

[56] References Cited

U.S. PATENT DOCUMENTS

| | | |
|---|---|---|
| 3,865,726 | 2/1975 | Chibata et al. . |
| 3,963,613 | 6/1976 | Chibata et al. . |
| 4,248,704 | 2/1981 | Marconi et al. ................. 210/632 |
| 4,356,267 | 10/1982 | Callegaro et al. . |
| 4,361,484 | 11/1982 | Larsson et al. .................. 210/632 |
| 4,450,153 | 5/1984 | Hopkins . |
| 4,692,411 | 9/1987 | Ghose . |
| 4,696,670 | 9/1987 | Ohnishi et al. . |
| 4,708,713 | 11/1987 | Lentz .................................. 604/5 |
| 4,846,786 | 7/1989 | Freed et al. ......................... 604/4 |

OTHER PUBLICATIONS

Pages vi through 103 of book entitled "Enzymes as Drugs" edited by John S. Holcenberg of the Medical College of Wisconsin and Joseph Roberts of Sloan Kettering Institute for Cancer Research dated Jan. 1981.

*Primary Examiner*—Alan W. Cannon
*Attorney, Agent, or Firm*—Trask, Britt & Rossa

[57] ABSTRACT

A new therapy for cancer which involves removal from circulation of several nonessentials amino acids, some essential amino acids and folic acid simultaneously and continuously for long-term therapy is disclosed. The therapy uses extracorporeal blood circulation using a multi-enzyme bioreactor without any of the side effects associated with the direct intravenous infusion of these enzymes. The combined depletion of folates and essential and nonessential amino acids produces a synergistic effect in treating the cancerous tissue, and serves to minimize or reduce the adaptation process of cancer cells, especially over a longer range continuous therapy.

5 Claims, 2 Drawing Sheets

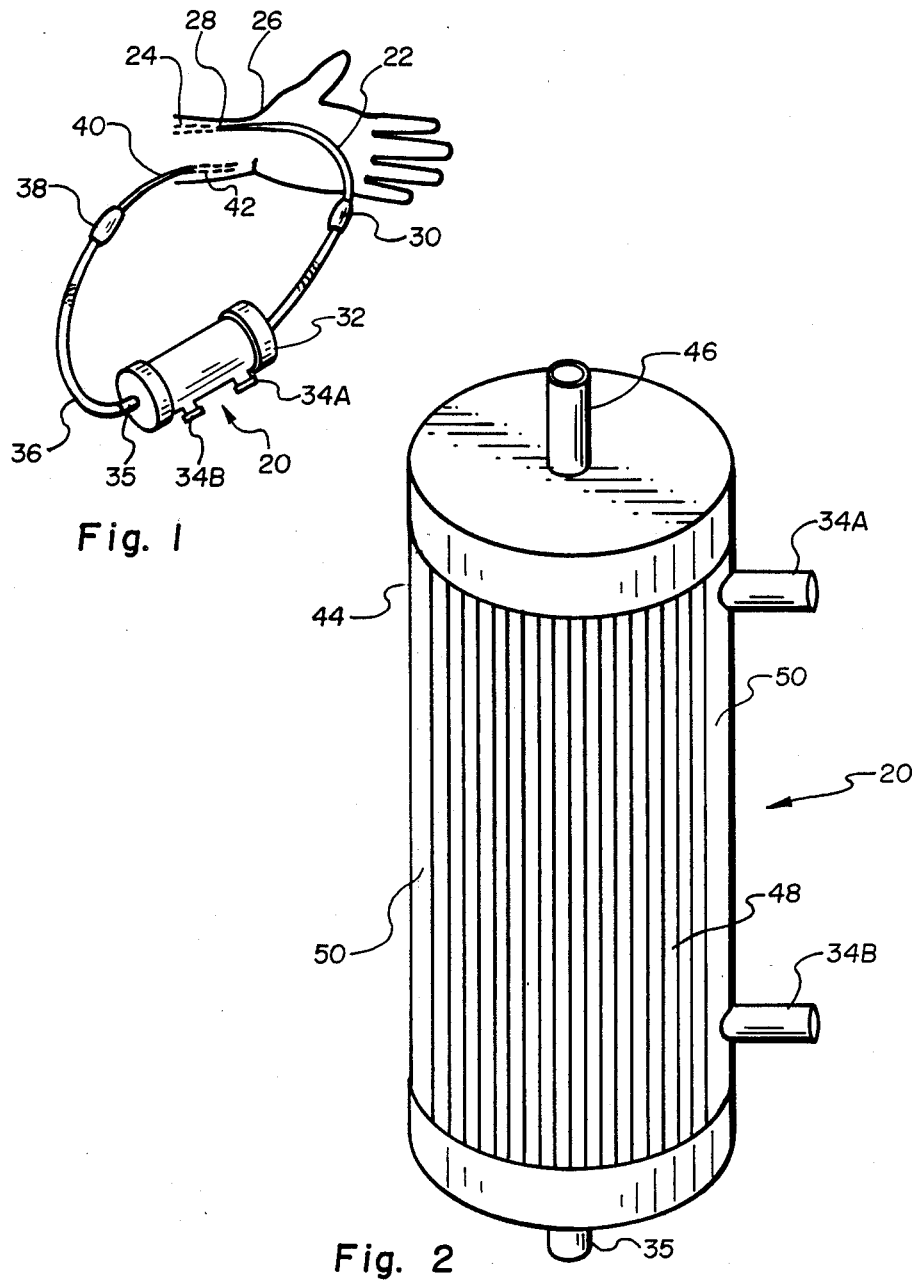

MULTI-ENZYME BIOREACTOR THERAPY FOR CANCER

BACKGROUND OF THE INVENTION

Cross-Reference to Related Application

This application is a continuation-in-part of applicant's copending application Serial No. 220,544 filed July 18, 1988, pending the contents of which are incorporated by this reference.

Field

This invention relates to a device and method for the removal of selected amino acids and folates from a fluid such as blood.

State of the Art

Noncancerous cells can synthesize nonessential (dispensable) amino acids when they are not available in an animal's blood. However, certain tumor cells cannot synthesize these nutrients in sufficient quantities, since they lack enzymes to catalyze their synthesis. Enzyme therapy depletes these amino acids and selectively kills the tumor cells. Under stressful conditions such as enzyme therapy, the tumor cells may develop the ability to synthesize the missing amino acid(s) and thus become resistant to the deprivation therapy. Such a phenomenon has been observed in asparaginase-sensitive leukemias which later become resistant to enzyme treatment.

Of the nonessential amino acids depleted with enzyme therapy, asparagine, glutamine, cysteine, ornithine and citrulline are the preferred candidates for enzymatic depletion therapy. Synthesis of these amino acids in various tumor tissues and the therapeutic enzymes for their depletion have been reviewed by the prior art. Asparaginase (ASE) in soluble form has been sequentially combined with methotrexate (MTX) to treat refractory acute leukemia to yield an overall 40% (31 patients out with 71 patients) complete remission (CR) of 10 weeks of therapy. The response rate was 35.5% in acute non-lymphocytic leukemia (ANLL) and 58.8% in acute lymphocytic leukemia (ALL). Asparaginase sequentially combined with high dose ARA-C (HIDAC) therapy of 30 patients gave 30% CR in ANLL, 30% CR in ALL, and 62% CR in lymphoma patients including central nervous system (CNS) disease.

Asparaginase in the treatment of 55 non-Hodgkin's lymphoma patients yielded a response rate of 50% with 8% CR and 42% partial remission (PR). In a randomized controlled study of 72 non-T cell ALL children, 36 received vincristeine, prednisone and doxirubicin. The other 36 received, in addition to these drugs, a weekly high dose of ASE. The ASE treated group responded better to therapy. Vincristeine, MTX and ASE regimen for 38 ALL patients resulted in 33% CR at 1 year, 10% continued in CR greater than 2 years.

In non-small cell lung cancer, ASE combined with MTX was not found to be useful. Excessive CNS toxicity was observed when adult leukemia patients were treated with succinylated Acinetobacter glutaminase-asparaginase (AGA) and no patient achieved CR or PR. Intraperitoneal administration of AGA plus melphalan achieved CR in one patient with ovarian carcinoma and peritoneal studding, but two other patients with Ehrlich ascites carcinoma did not respond. Cultured human pancreatic carcinoma cells (MIA PaCa-2) are sensitive to ASE.

Of the essential amino acids (those required in the diet of the host as well as the tumor), tryptophan and histidine are presently the best candidates for depletion therapy. Furthermore, since mammalian cells do not synthesize tryptophan, and histidine, tumor resistance to this therapy is not expected to occur. Enzyme-mediated tryptophan depletion resulted in marked inhibition of a variety of tumors (carcinoma, sarcoma, hepatoma, mastocytoma) in mice. Histidine depletion by histidase was also effective against Ehrlich ascites carcinoma (93% reduction) and Meth A ascites sarcoma (77% reduction).

Inhibitors of nucleotide biosynthesis are very toxic to cells, especially rapidly growing cells such as tumors or bacteria, because interruption of the supply of any class of nucleotides seriously limits the cell's capacity to synthesize the nucleic acids necessary for protein synthesis and replication. There are several types of inhibitors of nucleotide biosynthesis, each type acting at different points in the pathways of purine or pyrimidine nucleotides. Methotrexate (MTX) is one of the most widely used folate (folic acid) degradation agents for the treatment of leukemia, Burkitt's lymphoma and choriocarcinoma. Depletion of folic acid either by dietary control or by intravenous (i.v.) administration of carboxypeptidase G1 was shown to inhibit leukocyte proliferation transiently. Depletion of folates by dietary control is a very slow process and inefficient. As carboxypeptidase G1 (92,000 Daltons) is immunogenic, an intensive i.v. therapy with this enzyme is not possible. Hence, carboxypeptidases has been immobilized on hollow fiber nylon tubes and used extracorporeally.

These enzymes, injected in soluble form, although useful in principle, have many drawbacks in practice. Generally, these enzymes, being of heterologous origin, are recognized as such by the body and repeated applications may therefore result in adverse immunological reactions. Furtheremore, any enzymes intended for parenteral use must be highly purified to remove endotoxins and other contaminants. Injection of such purified proteins usually results in rapid removal by the reticuloendothelial system or destruction by the action of the body's proteolytic enzymes. Complications with intravenous infusion of L-Asparaginase (L-ASE) enzyme are acute encephalopathy; thrombotic and hemorrhagic condition, protein C deficiency; pancreatic pseudocyst formation; anaphylaxis reactions; inhibition of Antithrombin III, plasminogen and fibrinogen synthesis; and induction of hypercoagulable state which could lead to fatal pulmonary embolism; abnormalities in coagulation control; immune hemolytic anemia; transient secondary hypothyroidism; and suppression of erythropoiesis.

In order to overcome the above complications, L-ASE has been used in soluble adducts of L-ASE that can greatly increase the biological half-lives and reduce its immunogenecity. For example, L-ASE has been bound to polyethylene glycol, to albumin and to dextran. However, immunogenecity has not been eliminated completely and the increase in half-lives are modest. Encapsulation isolates the enzyme from the host's immune systems and also offers the potential for targeting the enzyme to specific tissues. L-ASE imbedded in autologous red blood cells was shown to be less toxic in monkeys than the free enzyme. Enzymes were also coupled to hollow fiber membranes and resins. Plasma was separated from blood extracorporeally, and only the plasma was perfused through the immobilized enzyme (Asparaginase-cellulose reactor). The clearance of asparagine in such a system cannot be greater than the plasma separation rate, which is normally not more than 30% of blood flow rate. This system is complex, expensive, and not suitable for continuous application for several days. Besides, this treatment was given only for a short period which resulted in a decrease in asparagine level followed by a gradual increase. Asparaginase was also immobilized on the dialysate side of the membrane dialyzer by reverse ultrafiltration followed by glutaraldehyde cross linking. The clearance obtained by this system was only 25 ml/min.

Drawbacks to therapy with immobilized L-ASE are (i) decrease in its activity, (ii) leaching of the bonded enzyme, (iii) unpredictable kinetics due to the adhesion of platelets and granulocytes to the immobilized enzyme, (iv) problems of sterilization, (v) requirement of a surgical procedure (extracorporeal blood circulation), and (vi) the high cost. In summary, enzymatic depletion therapy has great potential in the eradication of cancer cells, but toxic effects still exist and of resistance emerges to the therapy. Although the toxic effects are eliminated by the immobilization of the enzyme, this extracorporeal therapy was designed only for a short period of 4 to 6 hours which would give a "sawtooth" type of change in asparagine level, causing no clinical benefit. Moreover, these enzyme reactors were designed to deplete only one or two nonessential amino acids which may not offer "adequate" toxicity to cancer cells.

Various devices are available for the removal or chemical alteration of various chemicals in blood. Those disclosed in U.S. patents include:

In U.S. Pat. No. 4,696,670 to Ohnishi et al., plasma is separated from blood, and plasma is perfused through a column of immobilized enzymes for the removal of low density lipoproteins. Enzymes are immobilized by a chemical binding method. A complex switching mechanism is used for its operation.

U.S. Pat. No. 4,692,411 to Chose removes antigens or antibodies or any other biological cell from blood by agglutinating the species using a biochemical reaction technique followed by filtration to remove the agglutinated species.

In U.S. Pat. No. 4,450,153 to Hopkins, alcohol is removed from blood using an enzyme (alcohol oxidase) by circulating blood through a membrane dialyzer. The enzyme is mixed with a dialysate and used on the dialysate compartment of the dialyzer. This technique is the same as that of Marconi et al. and Chibeta et al.

In U.S. Pat. No. 4,361,484 to Larsson et al., the inventors immobilized an enzyme or an antibody or protein A in the pores of a membrane facing away from the blood phase by a chemical binding method. Using an oscillating pressure technique, plasma or fluid was forced in to and out of the membrane to achieve a high degree of convective mass transport.

In U.S. Pat. No. 4,248,704 to Marconi et al., an enzyme was trapped in a hollow fiber membrane to remove phenylalanine from the blood. Note that the same technique is used by Hopkins and Chibeta et al.

U.S. Pat. No. 3,963,613 to Chibeta et al., used aspartase for the removal of ammonia, and asparaginase for the removal of asparagine. Enzymes were mixed with a dialysate and used in the dialysate compartment. This technique has been adopted by others (see Hopkins, Marconi et al.).

In U.S. Pat. No. 3,865,726 to Chibeta et al., an enzyme is trapped in microcapsules by a chemical method. The microcapsules have a semipermeable membrane. Problems with such microcapsules include the fact that the capsules may break, spilling their contents into blood, they need to be sterilized, they cannot be reused, and the enzyme may become deactivated due to the chemicals used.

U.S. Pat. No. 4,356,267 to Callegaro et al. discloses an enzyme immobilized by a chemical binding method on the blood side of the membrane. Such an immobilization technique is prohibitively expensive and may even deactivate the enzyme. Furthermore, the enzyme may leach out.

None of these prior art techniques effectively combat the problem of "adaptation learning" by cancer cells. Adaptation learning is a problem analogous to resistance emergence in antimicrobial therapy. After being treated with a certain method, the cancer cells adapt and become immune to the therapy.

SUMMARY OF THE INVENTION

The invention includes a method of depleting essential and nonessential amino acids and folates from a fluid. The method and disclosed structure can be used to treat a cancer which is dependent on the presence of essential and nonessential amino acids and folates. This method includes first tapping into a cancerous animal's circulatory system with auxiliary circulatory path means through auxiliary circulatory path. Then, the blood is passed from the animal's circulatory path means. Next, the blood is passed from the animal's circulatory path through means (a "bioreactor") for altering the chemical structure of the essential amino acids, nonessential amino acids, and folates upon which the cancerous cells are dependent. The bioreactor is incorporated into the auxiliary path means and contains enzymes capable of altering the essential amino acids, nonessential amino acids, and folates contained within the blood. The blood, depleted of these constituents, is then returned to the circulatory system of the animal through the auxiliary circulatory path means. The treatment is preferably of a long duration, and can be continuous, lasting anywhere from days to several weeks.

In one embodiment the blood or other fluid is monitored regularly to determine the status of the patient.

A key to the therapy is the synergistic combination of depleting both nonessential and essential amino acids and folates from the blood stream or circulatory system of the animal affected thereby, thus denying key nutrients to the cancerous cells. With such treatment it is extremely unlikely that the cancerous cells can mutate or develop to synthesize all of the missing nutrients normally supplied by the victim's blood. Such a treatment overcomes the drawback of the existing therapies, which allows for the cancerous cells to "learn" to adapt themselves to the hostile environment, thus becoming resistant to the therapy.

The preferred continuous therapy of the present invention accentuates the treatment because the levels of missing nutrients do not rise back to "normal" values until after the treatment is halted. This overcomes the drawbacks of the prior art which only allowed for treatment times measured in hours, allowing the cancerous cells to adapt to the hostile environment, thus rendering the previously successful treatment useless the next time the cancer flares up.

A bioreactor of the present invention includes a filter fiber bundle comprising hollow fibers having ends connected one to another to form a loose midportion. The hollow fibers have open ends through which a fluid, such as blood, may pass. The filter fiber bundle is contained within a housing and the hollow fibers have a semipermeable portion in proximity of, or in communication with, the loose midportion through which some essential and nonessential amino acids and folates may pass. A dialysate chamber is contained within the housing in communication with the loose midportion of the filter fiber bundle. The dialysate chamber contains a solution having enzymes capable of altering essential and non-essential amino acids and folates. An inlet is arranged to direct fluid from outside the housing to contact the end of the filter fiber bundle and is further arranged to pass the fluid into the open ends and through hollow fibers. An outlet is arranged to receive fluid passing through the hollow fibers and pass it through to the exterior of the bioreactor. Fluid directed through the inlet flows through the hollow fibers and essential and nonessential amino acids and folates contained within the fluid permeate through the semipermeable portion of the fibers into the solution. Once within the solution, these nutrients interact with the enzymes contained within the solution and are altered by the enzymes to a chemical structure to less nutritional value of the cancerous cells. The altered nutrients are returned to the blood through the semipermeable portions of the fibers and pass with the other blood through the hollow fibers and through the outlet to exterior the bioreactor.

The bioreactor may further include means for removing, replacing and refilling the solution from the dialysate chamber such as ports contained within the housing. These ports can be sealed off to contain the fluid with a cap, cork, wax or other means. The bioreactor may be formed from any material capable of maintaining structural integrity, including biocompatible materials such as polycarbonate. In one embodiment, all of the hollow fibers are semipermeable.

A bioreactor will usually be structured with a plurality of hollow fibers comprising a filter fiber bundle. These fibers are attached to one another near their respective ends, e.g. by compressing or gluing. In the midportion of the bundle, between the respective ends, no glue or other attachment means is present, and the individual fibers are unattached. The hollow fibers are placed within a housing, and at least one of the hollow fibers has a semipermeable midportion. The space between the loose midportion and the housing defines a "dialysate chamber" or "dialysate compartment." Ports may communicate with the dialysate chamber or compartment for replenishment or replacement of the enzyme-containing solution contained therein. An inlet is arranged to direct fluid containing the amino acids and folates to be depleted to a first end of the housing. The fluid introduced into the bioreactor passes through the inlet, enters the end of the individual fibers of the filter fiber bundle at the first end of the housing and passes through the ends of the fibers. An outlet is arranged at the opposite or second end of the housing to receive fluid passing through the fibers. Amino acids and folates ("nutrients") permeate through the membrane and into the enzyme-containing solution The enzymes in the solution alter their respective amino acids and folates, thus depleting them from the solution. The altered nutrients permeate back through the membrane and are dissolved into the fluid passing therethrough. In the case of a bioreactor connected into an animal's circulatory system, the blood containing the altered amino acids may be returned to the animal.

The bioreactor can be used to deplete several nonessential and essential amino acids and folates continuously and simultaneously.

BRIEF DESCRIPTION OF THE DRAWINGS

FIG. 1 is a stylized representation of a bioreactor in use;

FIG. 2 is a side view of a preferred bioreactor for use in the invention;

DETAILED DESCRIPTION OF THE PREFERRED EMBODIMENT

Figure 3:
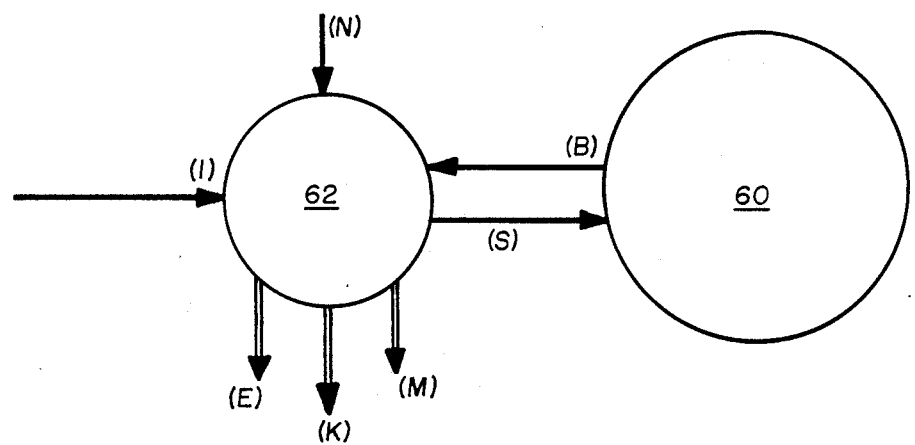
FIG. 3 depicts a two pool model for estimating whole body amino acid metabolism.

The prior art depleted only one or two key nutrients of cancer cells intermittently and tumor cells developed resistance to their therapy. The present invention is designed to prevent the build up of resistance against the depletion therapy by cancer cells. For this reason, cancer cells may be attacked with a greater intensity by depleting not only a plurality of nonessential amino acids but also selected essential amino acids e.g. (tryptophan or histidine) and folates simultaneously and continuously for a period generally greater than two weeks. Tryptophan, histidine and folates are essential for both the normal and the cancer cells. However, since the cancer cells grow rapidly, they may need these nutrients more than the normal cells, and hence they theoretically should be most affected by the depletion therapy.

Anaphylactic reactions, antigenicity and toxic effects associated with the injection of soluble enzymes are decreased since these enzymes are not in direct contact with the blood. Also, enzyme degradative products can be removed from the enzyme solution using known techniques such as ion-exchange columns.

Change in activity of enzymes is minimal since the enzymes are not subjected to any chemical modification or irreversible binding. The enzyme mixture may be reused by transferring it from one dialyzer to another fresh dialyzer.

In general, purification of enzymes is a complicated and expensive procedure. The enzymes used in the present system need not be as pure as with the prior art systems. Large molecular weight impurities (above 50,000 Daltons) preferably do not cross over into blood phase and the lower molecular weight impurities can be removed simply by dialysis. The problems associated with sterilizing enzymes are also eliminated.

Continuous heparinization of the system is possible by injecting the required amount of heparin into the enzyme solution intermittently. Since the molecular weight of heparin (10,000 to 30,000 Daltons) is below the molecular weight cut off of preferred semipermeable membranes, it can be allowed to diffuse into the blood phase. It should be noted that in such a case, the concentration of heparin at the membrane-blood interface will be much higher than in the bulk of the blood, which is desired to minimize the problems of blood clotting and thrombus formation. Such a system eliminates the need for a heparin pump and permits the system to be wearable.

The device may be made simple and wearable by a patient for continuous use.

Antineoplastic or other medications can also be injected into the enzyme solution to provide combined therapy. These medications will diffuse gradually into the blood phase at a controlled rate, thus avoiding toxic effects associated with the bolus injections of such drugs.

An extracorporeal multi-enzyme reactor has been designed, having fewer toxic effects and continuously depleting several key nutrients of cancer cells. FIG. 1 depicts the bioreactor generally 20 in use in a Quinton-Scribner shunt. An arterial line 22 is preferably placed within an artery 24 of the non-dominant forearm 26. A 16-gauge dialysis catheter 28 is used for blood access. An arterial blood sleeve 30 may be incorporated into the arterial line 22. Blood courses through the line 22 to the bioreactor 20. The depicted bioreactor 20 is a hollow fiber dialyzer 32 having its dialysate ports 34A, 34B sealed with caps or other means after having been filled with an enzyme solution. After passing through the bioreactor 20, the reacted blood passes through an outlet 35 into venous line 36, through venous blood sleeve 38 and male adapter 40 into a vein 42 in the forearm 26.

The bioreactor 20 depicted in FIG. 2 is a hollow fiber dialyzer commonly used in dialysis procedures. The bioreactor 20 includes an elongate housing 44 having an inlet 46, an outlet 35 and may have ports 34a and 34b. The housing 44 contains a filter fiber bundle 40 including at least one hollow filter fiber with a first open end, a second open end, and an intermediate semi-permeable wall portion proximate or in communication with the dialysate compartment 50. The first and second open ends are sealably mounted within the housing at the inlet and outlet respectively. The housing encloses a volume and defines a dialysate compartment 50 around the intermediate portion of the filter fiber bundle. The bioreactor 20 is constructed so that fluid, such as blood, entering the inlet passes into the first open end of the hollow filter fiber and through the fiber. A permeable portion of the fluid (e.g. a filtrate of diffusate) permeates the semi-permeable portion of the fiber.

The dialysate compartment 50 contains a solution. This solution contains enzymes selected to react with the permeable portion of the fluid passing through the semipermeable fibers.

The solution contained within the dialysate compartment 50 will preferably not initially include the chemicals which are to be altered by the bioreactor. The arterial blood or other fluid passing through the bioreactor 20 will include these chemicals. As such, a concentration gradient is created between the solution contained within the dialysate compartment 50 and the fluid contained within the "blood side" (i.e. inside the fiber) of the fibers. When a concentration gradient exists across a semi-permeable membrane such as the fibers are made of, molecules of the chemicals tend to migrate from areas of high concentration to areas of low concentration; i.e., chemicals which can permeate the fiber do permeate the fiber to the area of lower concentration.

Membranes for use in the fibers are chosen to allow selected chemicals to pass from the blood side of the fibers of the bioreactor 20 to the dialysate compartment 50.

The solution within the dialysate compartment contains enzymes selected to react with the chemicals passing through the fibers. Preferably, enzymes which are macromolecules too large to pass through the membrane are selected so that the solution need not be replenished with enzymes.

The bioreactor 20 depletes amino acids and folates from a fluid which passes through it. What particular amino acids and folates are depleted is dependent upon the particular enzymes chosen to be in the solution contained within the dialysate compartment 50.

When used to treat cancer victims, the enzymes chosen will preferably be tailored to treat the particular cancer involved. The enzymes are preferably water soluble and soluble in solutions such as normal saline. The enzymes further will preferably not denature or otherwise degrade under conditions in which the bioreactor operates. For example, the enzymes should be stable at relatively neutral pH (e.g. from about 4 to about 8) and will preferably not degrade at temperatures between room and body temperature.

The enzymes preferably do not permeate through the semi-permeable portion of the fibers of the filter fiber bundle 48. Since enzymes are generally macromolecular proteins, this can be accomplished by using relatively small pored semipermeable membrane in the bioreactor. Such a construction of the bioreactor decreases the likelihood of adverse immune reactions such as the development of allergies to the enzyme when the bioreactor is used with a living subject's blood.

In treating cancer within the teaching of this invention, enzymes will be chosen which alter folic acid derivatives ("folates") and both essential and nonessential amino acids so that they can no longer be used by the cancerous cells, thus "starving" them. In any event, they die. This synergistic effect of the combined depletion of both essential and nonessential amino acids and folates to minimize or reduce the adaptation process of cancer cells has not heretofore been recognized in the art.

Membranes suitable for the bioreactor are semipermeable. They allow the particular amino acids and folate to be depleted to pass, but are preferably impermeable to the passage of the chosen enzymes.

A particularly preferred membrane is Hemophan (a large membrane surface area dialyzer (1 $m^2$ surface area) with a molecular weight cut off of 30,000 Daltons, from Enka Glanzstoff, West Germany), which is a new membrane for dialysis, manufactured by a minor but specific chemical modification of cellulose, which displays excellent biocompatibility properties. The modification was performed by introducing tertiary-aminogroups into some of the cellobiosic units of the cellulose molecule. Hemophan displays very low levels of complement activation.

Less preferred membranes include Cuprophan, derived from cellulose, which often appears in the literature as a standard or reference for other dialyzer membranes and cellulosic membranes (Cuprophan, cellulose acetate). These are less preferred because they have been blamed for transient leukopenia and hypoxemia due to activation of complements by the cellulosic membranes. Essential amino acids upon which the particular cancer is dependent are candidates for enzymatic depletion therapy. Of the essential amino acids, tryptophan and histidine are the best candidates for depletion therapy.

All nonessential amino acids are candidates for the enzymatic depletion therapy. As used herein, the nonessential amino acids include:

| alanine | arginine | aspartic acid | asparagine |
|---|---|---|---|
| citrulline | cysteine | glycine | glutamic acid |
| glutamine | ornithine | proline | serine |
| | | | tyrosine |

Of these amino acids, asparagine, glutamine, cysteine, ornithine and citrulline are excellent candidates for the enzymatic depletion therapy.

Asparagine can be depleted by asparaginase derived from *E. Coli*, *Erwina cartovora* or *Citrobacter freundii*. These asparaginase have molecular weights in the range of 140,000 and their Michaelis-Menten constants ($k_m$) are around 10 to 50 μM. The specific activity of the purified enzyme is 133–700 IU/mg protein. They possess approximately 0.015%–9% glutaminase activity.

asparagine $\xrightarrow{\text{asparaginase}}$ aspartate + NH$_3$

Glutamine can be depleted by glutaminase and glutaminase-asparaginase.

glutamine $\xrightarrow{\text{glutaminase}}$ glutamic acid + NH$_3$

However, the $k_m$ of glutaminase (*E. Coli*) is very high (3,000 μM), whereas glutaminase-asparaginase derived from Pseudomonas (PGA) and Acinetobacter (AGA) both have a very low $k_m=4$ to 5 μM for glutamine. Hence, either AGA or PGA is preferably used. *E. Coli* asparaginase also has activity for glutamine conversion, 3 to 5%. The activity of AGA for asparagine and glutamine is about the same. However, AGA is much more efficient in removing glutamine, which is present in plasma in at least a ten-fold excess over asparagine. For this reason, it is better to combine *E. Coli* asparaginase with AGA. Otherwise, glutaminase should be used in large amounts (for example 5,000 units instead of 150 units).

Arginine, ornithine, and citrulline have interrelated biosynthetic pathways. In tissues, arginine is believed to be broken down to ornithine by two different routes. One provides a mechanism for urea formation. The other route is one that provides a source of energy for many microorganisms (arginine dihydrolase pathway). Arginine is biosynthesized from ornithine via citrulline. Therefore, for broad antitumor efficacy, enzyme therapy may have to deplete arginine, ornithine, and citrulline.

All tumors except hepatomas are believed to require citrulline or arginine for growth. Citrulline can replace the arginine requirement in most tumors. Some tumors lack urea-cycle enzymes and may be sensitive to depletion of arginine or citrulline in the blood. Since ornithine can be converted to citrulline only in the liver, depletion of ornithine in blood may decrease the availability of ornithine for the synthesis of growth-regulating polyamines. Ornithine is the only precursor for mammalian polyamine synthesis. Ornithine can be converted to citrulline enzymatically by ornithine transcarbamoylase (400,000 Daltons; $k_m=10$ μM).

For broad antitumor efficacy, enzyme therapy may have to deplete both arginine and citrulline. The most promising enzymes available are arginine deiminase with $k_m=4$ μM (80,000 Daltons) from *S. faecalis*, chemically modified mammalian arginase, and arginine decarboxylase with $k_m=0.15$ μM (300,000 Daltons). Arginine deiminase catalyzes the hydrolysis of arginine to citrulline and ammonia. This enzyme may be very effective in the treatment of tumors that both require arginine and cannot utilize citrulline. Arginine decarboxylase catalyzes the degradation of arginine to agmatine and carbon dioxide. These enzymes may have broader antitumor effect if combined with arginine and citrulline analogs like canavanine, canaline and indospicine.

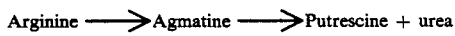

Arginine $\xrightarrow{\text{arginine decarboxylase + H}_2\text{O}}$ Agmatine $\longrightarrow$ Putrescine + urea Tryptophan has been depleted by about 35% in rodents by injecting a very high dose (10,200 IU/kg) of tryptophanase (*E. Coli*). Its molecular weight is 281,000. The poor activity of this enzyme was attributed to its requirement of exogenous pyridoxal phosphate as coenzyme. Also its $k_m=330$ is not very low. Whereas Indolyl-3-alkanehydroxylase (IAH) enzyme (250,000 Daltons) derived from Pseudomonas soil-isolate organism hydroxylates indole compounds, including tryptophan ($k_m=2.4$ μM) and serotonin, and it does not need any exogenous cofactors for activity However, IAH is presently not readily available commercially.

Tryptophan $\longrightarrow$ Indole + pyruvate + NH$_4$

Tryptophan $\xrightarrow{\text{IAH}}$

5-Hydroxytryptophan $\xrightarrow[\text{(5-Hydroxytryptoamine)}]{\text{decarboxylation}}$ Serotonin Instead of tryptophan, histidine can be depleted as discussed before. Histidine decarboxylase (195,000 Daltons; $k_m=1,000$ μM) is readily available from Sigma Chemical Company.

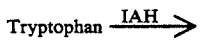
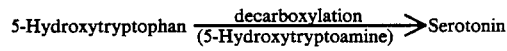

Histidine $\xrightarrow{\text{Histidine decarboxylase}}$ Histamine + CO$_2$

Carboxypeptidase G1 (from *Pseudomonas stutzeri*) hydrolyzes folic acid, methotrexate, and a number of peptides containing L-glutamic acid in the C-terminal. It utilizes leucovorin as the sole source of carbon and nitrogen. Its molecular weight is 92,000 and has a low $k_m=1.1$ μM.

folic acid $\xrightarrow{\text{Carboxypeptidase G1}}$ pteroic acid + glutamic acid In summary, some enzymes which may be included in the bioreactor are given in Table A.

TABLE A

Enzymes useful in the present bioreactor and their properties.

| Enzyme | mole weight (Daltons) | $k_m$ (μM) | $V_{max}$ | (uMole) (min./mg) |
|---|---|---|---|---|
| *E. Coli* Asparaginase | 130,000 | 10. | — | |
| Acinetobacter glutaminase-asparaginase (AGA) or gluminase (*E.Coli*) (if AGA not | 138,000 141,000 138,000 | 4.4–5.8 3,000 1,000 | — — | |

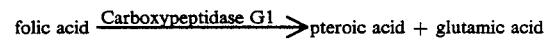

TABLE A-continued

Enzymes useful in the present bioreactor and their properties.

| Enzyme | mole weight (Daltons) | $k_m$ ($\mu M$) | $V_{max}$ | (uMole) (min./mg) |
|---|---|---|---|---|
| available) or glutaminase (if AGA is not available) | | | | |
| Arginine decarboxylase (E. Coli) | 300,000 | 0.25 | — | |
| Ornithine transcarbamoylase | 400,000 | 10.00 | — | |
| Indolyl-3-alkane-hydroxylase (S. faecalis) or Tryptophanase (E. Coli) if IAH is not available | 250,000 281,000 | 2.4 330 | — 26 | |
| Histidine decarboxylase (Lactobacillus 30a) | 195,000 | 1,000 | — | |
| Carboxypeptidase G1 (Pseudomonas Stutzeri) | 92,000 | 1.1 | 200–884 | |

The above enzymes, each in increments of 1000 Units may be dissolved in a phosphate buffer solution (about 300 ml is required to fill the dialysate chamber of a dialyzer) at pH 7.3. Except AGA, IAH and Carboxy peptidase G1, other enzymes are available from Sigma Chemical Company. Carboxy peptidase G1 is available from Biopure Corporation, Boston. IAH and AGA may be available from other sources (Memorial Sloan Kettering Cancer Center, New York). Otherwise, IAH and AGA may be replaced by tryptophanase and glutaminase from Sigma Chemical Company respectively. Glutaminase is generally used in large quantities.

A typical bioreactor may include the following enzymes:

(i) *E. Coli* Asparaginase for asparagine conversion;

(ii) *Acinetobacter* glutaminase-asparaginase (AGA) for asparagine and glutamine depletion;

(iii) Arginine decarboxylase for arginine depletion;

(iv) Ornithine transcarbamoxylase for ornithine depletion and;

(v) Carboxypeptidase G1 for folate degradation

Blood damage may be minimized by not using a blood pump. Blood can be propelled through the bioreactor using the arteriovenous pressure difference as the driving force. A sheep has obtained blood flow rates 300 to 500 ml/min. In humans, a direct arteriovenous fistula in the non-dominant forearm remains the preferred access route for maintenance hemodialysis. (FIG. 1) In many centers, the use of subclavian catheters is becoming the most widely used temporary vascular access, especially in children. In work involving sheep and dogs, a carotid artery-jugular vein shunt is surgically created and this shunt used for the extracorporeal blood circulation through the bioreactor.

Blood access in an animal may be done through a surgically created arteriovenous (carotid artery-jugular vein) fistula by the following standard surgical procedure:

Anesthetize the animal with sodium pentobarbital, 30 mg/kg and shave the neck and wash with Betadine ®. Cannulate the arterialized vein with Travenol 15 gauge hemodialysis catheters. Allow the blood from the arterial cannula to flow through the extracorporeal perfusion system by the arteriovenous pressure gradient and return the blood to the animal via a venous catheter inserted into the jugular vein on the right side Hyperextension of the animal's neck and digital pressure at the lowest visible portion of the fistulae expands the vessel and renders it more accessible for cannulation. Following insertion of needles, leave the catheters in place while they are flushed repetitively. When it appears that all bleeding around the needles had stopped, heparinize the animal fully (10,000 Units). After establishing the blood access, the animal is allowed to recover from the anaesthesia and stand in the animal cage. The needles will be properly bandaged to the neck and protected from accidental disengagement of needles and infection.

At the conclusion of the experiment, return all the blood from the extracorporeal system to the animal, and give the animal protamine (25 mg) intravenously. Withdraw the arterial needle and occlude the fistulae by digital pressure for 15 mins. to accomplish hemostasis.

After the bioreactor has been incorporated into the animal patient's circulatory system, blood courses through the bioreactor. Plasma and permeable components of the blood permeate the membrane to react with the "dialysate chamber" of the bioreactor. Inside the dialysate chamber, the dialysate solution includes the selected enzymes. These enzymes react with the animo acids and other chemicals with which they normally react changing their chemical structures to inactive forms. As used herein, "inactive forms" means those chemical structures which cannot be used as effectively as non-altered forms by the cancerous tissue.

A fresh dialyzer may be used daily, but the enzyme solution can be removed from the used dialyzer and injected into the "dialysate chamber" of the fresh dialyzer. The activity of the enzymes may be checked by taking a sample (e.g. 1 ml) of enzyme solution from the dialysate chamber while transferring it into the fresh dialyzer. If the enzyme solution is deactivated (e.g. due to denaturation or due to permeation of inhibiting substances into the dialysate chamber) a fresh enzyme solution can be installed.

Figure 4:
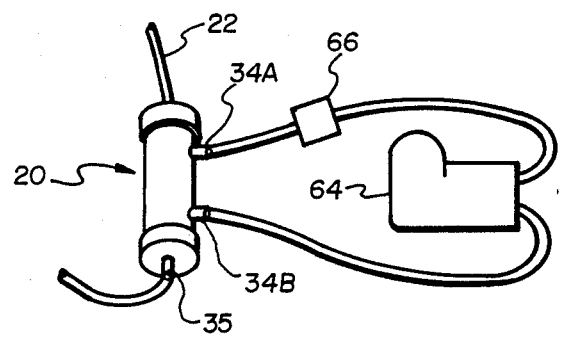
FIG. 4 is a perspective view showing the bioreactor of FIG. 1 in conjunction with a pump and means for removing enzymatic reaction products.

In one particularly preferred embodiment of the invention (FIG. 4), a pump 64 is connected to ports 34A, 34B in the housing which accesses the dialysate compartment of the bioreactor 20. The pump 64 recirculates the enzymatic solution into and out of the dialysate compartment. In this particular system other means 66 can be incorporated to remove the products of the enzymatic reactions (e.g. $NH_3$, $CO_2$, histamine, urea and putrescine) from the solution so that fewer potential toxins will enter the system. Such means 66 may include a dialyzer, other enzymes, or ion exchange columns or resins.

Those patients who respond to depletion therapy usually respond within a week. If the therapy is discontinued early, concentrations of nonessential amino acids will rise back to their normal values which may or may not have therapeutic value. Hence, the present bioreactor is preferably designed to operate continuously for a minimum period of two weeks. Experiments have shown that enzyme mediated depletion of selected essential amino acids for short periods of time (2 or 3 weeks) appears to be relatively well tolerated by tumor-bearing hosts. In these experiments, the weight of different organs (heart, brain, kidney, liver, spleen) were be recorded as a percentage of animal's body weight after terminating the therapy. Also, complete profile of animo acid levels in these tissues may be determined, indicating effects of this therapy on normal cells.

Monitoring of the system once incorporated into the patient's circulatory system may include hematological studies, coagulation studies, enzymology and biochemical or pharmacological studies, and oncological studies.

Hematological Studies

Chemistry: Electrolytes, enzymes, inorganic and organic constituents including ammonia and serum osmolality may be performed. Such tests include the following:

Electrolytes: sodium, potassium, calcium, chloride, $CO_2$, blood urea nitrogen (BUN), creatinine, uric acid and glucose.

Enzymes: Alkaline phosphatase, lactate dehydrogenase (LDH), serum glutamic oxaloacetic transaminase (SGOT), and serum glutamic pyruvic transaminase (SGPT).

Inorganic and organic constituents: uric acid, calcium, phosphorus, total protein, albumin, globulin, total bilirubin, direct bilirubin, iron, cholesterol, triglyceride, albumin/globulin ratio, BUN/Creatinine ratio and Osmolality.

Plasma free hemoglobin (PLHgb) may be monitored by spectrophotometry.

Cell Count: erythrocytes, leukocytes and platelets will be counted daily with the help of Coulton Counter (ZBI) following established protocols. Coulton counter may also be used for hematocrit (HCT) and mean cell volume (MCV).

Coagulation Studies

Activated clotting time (ACT) is preferably determined every three hours using a standard Hemachron meter. The heparinization will be adjusted to maintain the ACT value around 5 minutes. In order to minimize the problems of blood clotting on the membrane, a fresh membrane can be used every day. Heparin on the membrane surface so as to obtain a thromboresistance surface may be immobilized.

Prothrombin time (PT), partial thrombin time (PTT), complements C3, C4 and C5, and fibrinogen require 4.5 ml blood in a blue top citrate tube on ice sent to the analyzing laboratory. The PT and PTT determinations may be via standard laboratory techniques utilizing a modification of the Quick technique (type of clot detection) with an automated optical density coagulizer. The fibrinogen levels can be assayed by the Data-Fi commercial clotting time of dilute plasma in comparison with standard preparations Test blood may be withdrawn in sodium citrate, and this gel may be added to remove heparin prior to the performance of PTT test. Hepasorb TM marketed by General Diagnostics may also be used for removal of heparin form blood samples.

Quantitative Amino Acid Analysis

This analysis can be done by using an Amino Acid Analyser (High Performance Liquid Chromatography (HPLC) system).

Folate Analysis

Plasma levels of folates may be measured by *Lactobacillus casei* assay. This method has been described in detail in Herbert, V., "Aseptic Addition Method for *Lactobacillus casei* Assay of Folate Activity in Human Serum." *J. Clin Path.,* 19: 12–16, 1966, the contents of which are incorporated by reference to the extent they are necessary to this disclosure.

Stability of Enzymes and Analysis of Degradative Products

Enzyme activity may decrease during the therapy. This change in enzyme activity is preferably determined to know the extent of the enzyme solution is reusability in the bioreactor. Since these enzymes are in equilibrium with blood (separated by a membrane) reaction products (ammonia, aspartate, glutamate, threonine, pteroic acid, histamine, citrulline, agmatine, serotonin, glutamic acid and others) will diffuse back into blood phase and will be disposed of by the metabolic systems of the animal including the liver and kidney. The levels of these products in plasma pool and bioreactor may increase. The reaction product levels in plasma and in the bioreactor may also be determined.

Asparaginase and glutaminase activity may be measured by ammonia formation by direct nesslerization as described by Roberts et al, "Isolation, crystallization, and properties of Achromobacteraceae Glutaminase-Asparaginase with antitumor activity," *J.Biol. Chem.,* 242:84–90, 1972, the contents of which are incorporated by this reference to the extent they are necessary to this disclosure.

One unit of asparaginase releases 1.0 μmole of ammonium nitrogen from L-asparagine per minute at pH 8.6 at 37° C. One unit of glutaminase will deaminate 1.0 μmole of L-glutamine per minute at pH 4.9 at 37° C.

Carboxypeptidase activity: The change in absorbance that occurs when methotrexate is hydrolyzed to 2,4-diamino-$N^{10}$-methylpteroate provides a simple and direct measure of activity of carboxypeptidase G1. This method has been described in detail by McCullough, J. L., et al. "Purification and properties of Carboxypeptidase G1." *J. Biol. Chem.* 216:7207–7213, 1971, the contents of which are incorporated by this reference to the extent they are necessary for this disclosure.

Arginine decarboxylase activity may be assayed by determining the amount of carbon dioxide produced in a Warburg manometer. One unit of this enzyme will release 1.0 μmole of carbon dioxide from L-arginine per minute at pH 5.2 at 37° C.

Ornithine Carbamyltransferase activity may be assayed by measuring the amount of citrulline formed during the incubation for 5 minutes at 30° C. of a mixture containing: 20 μmol imidazole buffer at pH 7.,8 in a total volume of 2 ml. This method has been described by Stalon, V., et al., Regulation of the catabolic ornithine carbamoyltransferase of *Pseudomonas fluorescens. Eur. J. Biochem.* 29:25–35, 1972, the contents of which are incorporated by this reference to the extent they are necessary for this disclosure.

Tryptophanase activity: One mg of tryptophanase will release 15–40 μg of indole from L-tryptophan in 10 minutes at pH 8.3, 37° C. The enzyme will be assayed by the Nessler's determination for ammonia production as described in Roberts, et al., "Isolation, Crystallization and properties of Indolyl-3-alkane-alpha-Hydroxylase," *J. Biol. Chem.,* 252:2640–2647, 1977, the contents of which are incorporated by this reference to the extent they are necessary for this disclosure.

Histidine decarboxylase activity may be assayed by determining the amount of carbon dioxide produced in a Warburg manometer. One unit of this enzyme will release 1.0 μmole of carbon dioxide from histidine per minute at pH of 4.5 at 37° C.

Enzyme degradative products are ammonia, glutamate, aspartate, agmatine, alpha-hydroxytroptophan, pteroic acid, glutamic acid, histamine, citrulline, and others. They may be analyzed on a high performance liquid chromatography (HPLC) system.

Temperature (T) and pH of the enzyme solution will be very close to that of blood and they are not considered variables in this therapy. Hence, effects of T and pH on enzymatic reaction need not be considered in this work.

Pharmacokinetic Studies

The whole body can be considered as a simplified two-pool system (FIG. 3) containing an exchangeable free amino acid that is measured by the plasma compartment and a single protein pool 60. The basal values of protein breakdown (B), amino acid synthesis (S) and de novo synthesis (N) are available. The values of B and S for tumor cells are not known and they may be zero for some of the nonessential amino acids. However, during a long-term continuous depletion therapy, the values of B, S and N may change.

FIG. 3 also shows dietary intake (I); oxidation (E); depletion therapy (K); and oxidative metabolism (M) to and from the metabolic pool 62 of free amino acids. This model allows for the estimation of the whole body amino acid metabolism which is very useful for pharmacokinetic studies.

EXAMPLE 1

An extracorporeal multi-enzyme reactor with no toxic effects was designed which depletes continuously several key nutrients of cancer cells.

A theoretical analysis of the bioreactor was made to determine the effects of various design variables on the clearance of solutes. In a preliminary ex-vivo sheep study, blood was circulated continuously for three days through the bioreactor with multi-enzyme using a surgically created arteria-venous shunt. Arterial (inlet) and venous (outlet) blood was analyzed for amino acids.

A short-term evaluation of a bioreactor made according to the invention was performed using a normal sheep in the Artificial Heart Research Center, University of Utah. A functioning carotid artery-jugular vein external shunt was implanted into the sheep. Enzymes from the Sigma Chemical Co. including those listed in Table 1 were mixed in 300 ml of normal saline solution (0.1%) which was used to prime the dialysate compartment of a hollow fiber dialyzer (Travenol CF capillary flow dialyzer, 1.2 m$^2$ surface area, cuprophan membrane).

TABLE 1

| Enzymes used in an exemplary bioreactor. | | |
| --- | --- | --- |
| Enzyme | Quantity | $k_m(\mu M)$ |
| Asparaginase (E. Coli grade VIII) | 1,000 Units | 10.00 |
| Glutaminase (E. Coli grade II) | 150 Units | 3,000.00 |
| L. Arginine Decarboxylase (E. Coli type II) | 150 Units | 0.25 |
| Ornithine Carbamyl transferase (S. Faecalis) | 300 Units | 10.00 |

Carboxypeptidase G1 for the denaturation of folic acid is available from BioPure Corporation, Boston, Massachusetts and was used in this example. Since the $k_m$ of glutaminase is much greater than that of Acinetobacter glutaminaseasparaginase (AGA), AGA is preferred to glutaminase. AGA is available from the Sloan-Kettering Institute for Cancer Research. Tryptophanase is available from Sigma Chemicals Co. Pyridoxal phosphate is preferably used with the tryptophan as a coenzyme. Instead of depleting tryptophane, histidine can be depleted. Histidine decarboxylase ($km=1000$ $\mu M$, molecular weight=195,000) is also readily available from Sigma Chemical Company.

The dialysate compartment of the dialyzer was primed with the described enzyme solution. Heparin (10,000 Units) was also injected into this enzyme solution. The blood side of the dialyzer was flushed with 3 liters of sterile normal saline solution to remove all air bubbles. It was then primed with normal saline solution containing 5,000 Units heparin/liter. The arterial and venous blood lines were then connected to carotid artery and jugular vein cannulas of the shunt respectively.

Arterial (inlet to the bioreactor) and venous (outlet of the bioreactor) blood samples (20 ml) were required every 24 hours for a blood chemistry, hematology and amino acid analysis. Also, 1 ml of arterial blood was taken every 3 hours to determine the activated clotting time (ACT) of the whole blood using Hemacron meter. Heparin (10,000 units) was injected into the enzyme solution compartment every three hours. The heparin injection dose was adjusted to maintain ACT values in the range of 200 to 400 seconds.

Blood flow rate was measured by injecting an air bubble into the arterial line and measuring the time required for the bubble to travel through a known volume segment of the tubing. The initial blood flow rate was found to be about 350 ml/min, and this decreased to about 150 ml/min at the end of 24 hours of blood circulation. Because of this decrease, the enzyme solution was taken out of the bioreactor using a large syringe and transferred into a dialysate chamber of a fresh dialyzer every 24 hours of continuous extracorporeal blood circulation. The fresh dialyzer was flushed with normal saline and was then used to replace the "old" bioreactor. During this changeover, the arterial blood line was clamped and the bioreactor was flushed with 300 ml of normal saline so that most of the blood contained within the bioreactor would be returned to the animal. The venous line was then clamped and the "old" bioreactor disconnected from the circulation. The fresh bioreactor (primed with the normal saline solution on the blood side and the "old" enzyme solution on the dialysate side) was then connected to restart the extracorporeal blood circulation. The treatment was continued for three days and was electively stopped.

During the three days of continuous therapy, the animal's eating habits and body temperature remained normal. Table 2 shows the animal's daily hematology profile. There were no significant changes in red blood cells (RBC), platelets (PLT), white blood cells (WBC), hematocrit (HCT), hemoglobin (Hgb), mean cell volume (MCV), or plasma hemoglobin (Pl Hgb).

TABLE 2

| | Hematology Profile | | | | | | |
| --- | --- | --- | --- | --- | --- | --- | --- |
| Time (hrs) | RBC ($10^6$) | PLT ($10^3$) | WBC ($10^3$) | HCT(%) | Hgb (gm) | MCV (fl) | PL Hgb (mg/dl) |
| 0.1 | 9.24 | 140 | 3.4 | 32 | 11.0 | 33 | 0.1 |
| 24.0 | 11.10 | 210 | 9.5 | 39 | 14.0 | 32 | 1.1 |
| 48.0 | 11.70 | 220 | 9.7 | 40 | 14.0 | 32 | 1.2 |
| 72.0 | 11.60 | 180 | 9.8 | 38 | 12.4 | 33 | 1.5 |
| NORMALS | 8-16 | | 4-10 | 24-50 | 9-15 | 23-48 | 0 |

As shown by Table 3, there were no significant changes in the blood chemistry during the therapy.

TABLE 3

| | | | | Blood Chemistry Profile | | | | |
|---|---|---|---|---|---|---|---|---|
| Time (hrs) | SGOT SGPT U/L | Tot.Bil. Chol. mg/dl | BUN Creat mg/dl | Alk.Phos. GT IU/L | Ca PO4 mg/dl | Tot.Prot. LDH g/dl/IU/L | Alb. Glob g/dl | Uric Gluc mg/dl |
| 0.1 | 89/11 | 0/41 | 17/1.0 | 80/29 | 9.8/4.3 | 6.7/409 | 2.4/4.3 | .7/73 |
| 24.0 | 85/10 | 0/40 | 17/1.0 | 70/1. | 9/7.8 | 6.4/350 | 2.3/4. | 0/60 |
| 48.0 | 80/8 | 0/41 | 15/1.2 | 65/32 | 7.2/7/5 | 6.3/320 | 2.2/3.9 | 0/55 |
| 72.0 | 72/6 | 0/41 | 13/1.1 | 51/37 | 5.7/8.8 | 6/302 | 2.2/3.8 | 0/45 |
| NORMALS | | | | | | | | |
| | 68–90 | 0–0.4 | 10–30 | 5–30 | 5.7 | 4.9/7.7 | 2.4–3.8 | 0.2.9 |
| | 10–12 | 52–76 | 1–2 | — | 6.9 | 60–111 | 3.5–5.7 | 50–80 |

*SGOT = serum glutamic oxalactic transaminate; SGPT = serum glutamic pyruvic transaminate; Total Bil = total bilirubin; BUN = blood urea nitrogen; TOt.Prot. = total protein; Alb = albumin; Uric = Uric acid; gluc = glucose; Chol = cholesterol; Creat = creatinine; LDH = lactate dehydrogenase; Glob = globulin A theoretical analysis of the bioreactor was made to determine the effects of various design variables on the clearance of solutes. In a preliminary ex-vivo sheep study, blood was circulated continuously for three days through the bioreactor with multi-enzyme using a surgically created arteria-venous shunt. Arterial (inlet) and venous (outlet) blood was analyzed for amino acids. The results are encouraging (see Table 4), and there were no side effects. Future studies involve optimization of the system and depletion of folates and tryptophan simultaneously.

Table 4 shows the change in amino acid levels of arginine, asparagine, glutamine and ornithine in plasma at the inlet (arterial) and the outlet (venous) of the bioreactor during three days of continuous extracorporeal blood circulation.

TABLE 4

Amino acid levels ($\mu$mole/l) in plasma at inlet and outlet of the bioreactor

| Time (hrs) | Arginine | | Asparagine | | Glutamine | | Ornithine | |
|---|---|---|---|---|---|---|---|---|
| | Inlet | Outlet | Inlet | Outlet | Inlet | Outlet | Inlet | Outlet |
| 0.1 | 397 | 283 | 41 | 6 | 408 | 249 | 208 | 72 |
| 1 | 182 | 182 | 6 | 0 | 251 | 185 | 226 | 340 |
| 24 | 0 | 0 | 25 | 0 | 349 | 299 | 133 | 0 |
| 72 | 0 | 0 | 50 | 0 | 416 | 437 | 191 | 49 |

Table 4 shows that arginine, asparagine and ornithine in plasma were depleted to almost zero level and maintained at this low level for three days until the termination of the treatment. No measurement of change in activity of the enzymes in the solution was made. However, the fact that the level of these amino acids remained low until the end of the experiment, indicates that these enzymes did remain sufficiently active.

The depletion of glutamine was not as successful in this particular experiment. This may be due to the high value of $k_m$ of glutaminase or to the relatively low amounts of glutaminase used in the bioreactor (see Table 1). This problem can be solved by using acinetobactes glutaminaseasparaginase (AGA) instead of glutaminase in large amounts.

In summary, this example shows that it is feasible to deplete several amino acids and maintain their level in plasma at a very low level continuously for three days without any observable side effects. This bioreactor can be used to deplete any number of amino acids in the plasma and it is limited only by the availability of the enzymes with low values of $k_m$.

Reference herein to specific details or certain embodiments is not intended to limit the scope of the appended claims.

What is claimed is:

1. A method of simultaneously depleting essential amino acids, nonessential amino acids, and folate from a fluid comprising:
   shunting said fluid through means for altering the chemical structure of the essential amino acids, nonessential amino acids, and folates thus depleting said essential amino acids, nonessential amino acids, and folates from said fluid.

2. The method of claim 1 wherein said means for altering the chemical structure of the essential amino acids, nonessential amino acids, and folates is a bioreactor having an inlet for receiving a fluid containing essential amino acids, nonessential amino acids, and folates; a filter fiber bundle having at least one semipermeable fiber through which amino acids and folates may pass; a housing which forms a dialysate chamber; a solution contained within said dialysate chamber, said solution containing enzymes capable of altering said amino acids and folates; and an outlet for directing said fluid exterior said bioreactor.

3. A method of treating a cancer which is dependent on the presence of essential and nonessential amino acids and folates comprising:
   tapping into the circulatory system of an animal having the cancer with auxiliary circulatory path means;
   passing blood from the animal through means for altering the chemical structure of essential amino acids, nonessential amino acids, and folates, said means incorporated into said auxiliary circulatory path means;
   depleting a portion of the essential amino acids, nonessential amino acids, and folates contained within said blood by altering their chemical structures with enzymes; and
   returning the depleted blood to the circulatory system of the animal through the auxiliary circulatory path means.

4. The method of claim 3 wherein said treatment is continuous and lasts at least two weeks.

5. The method of claim 4 wherein said blood is monitored to determine the status of health of the animal.

* * * * *

UNITED STATES PATENT AND TRADEMARK OFFICE
CERTIFICATE OF CORRECTION

PATENT NO. : 4,955,857

DATED : September 11, 1990

INVENTOR(S) : Udipi R. Shettigar

It is certified that error appears in the above-identified patent and that said Letters Patent is hereby corrected as shown below:

In the Abstract, line 2, delete last "s" on --nonessentials--.

Column 1, line 41, change "of" to --with--;
Column 4, line 32, change "Then" to --Next--;
Column 4, line 34, change "Next" to --Then--.

Column 5, line 62, add a comma after "housing".
Column 6, line 31, delete "e.g.".
Column 6, line 31, after "(" insert --e.g.--.
Column 7, line 31, after "35" insert --,--.
Column 9, line 6, delete "arginine".
Column 10, line 27, after "activity" insert a --.--;
Column 10, line 66, change "Acinetobacter" to --Acinetobacter--.
Column 11, line 19, change "Pseudomonas Stutzeri" to --Pseudomonas Stutzeri--.
Column 11, line 22, after "Units" insert --,--;
Column 11, line 67, after "side" insert --.--.
Column 13, line 48, after "preparations" add --.--.

Column 15, line 64, change "Acinetobacter" to --Acinetobacter--.

Column 17, line 55, change "acinetobactes" to --acinetobacter--;
Column 17, line 57, after "amounts" add --.--.

Signed and Sealed this

Second Day of March, 1993

Attest:

STEPHEN G. KUNIN

Attesting Officer

Acting Commissioner of Patents and Trademarks